(12) United States Patent
Simjee et al.

(10) Patent No.: US 9,272,998 B1
(45) Date of Patent: Mar. 1, 2016

(54) MODULATION OF C-FOS AND BDNF PROTEIN EXPRESSION IN PENTYLENETETRAZOLE-KINDLED MICE FOLLOWING THE TREATMENT WITH NOVEL ANTI-EPILEPTIC COMPOUND HHL-6

(71) Applicants: Shabana Usman Simjee, Karachi (PK); Sabira Begum, Karachi (PK); Saima Mahmood Malhi, Karachi (PK); Huma Jawed, Karachi (PK); Nadeem Ashraf, Karachi (PK); Farina Hanif, Karachi (PK); Bina S. Siddiqui, Karachi (PK); Farhat Zubair, Karachi (PK)

(72) Inventors: Shabana Usman Simjee, Karachi (PK); Sabira Begum, Karachi (PK); Saima Mahmood Malhi, Karachi (PK); Huma Jawed, Karachi (PK); Nadeem Ashraf, Karachi (PK); Farina Hanif, Karachi (PK); Bina S. Siddiqui, Karachi (PK); Farhat Zubair, Karachi (PK)

( * ) Notice: Subject to any disclaimer, the term of this patent is extended or adjusted under 35 U.S.C. 154(b) by 0 days.

(21) Appl. No.: 14/607,880

(22) Filed: Jan. 28, 2015

(51) Int. Cl.
  *C07D 209/14* (2006.01)
  *A61K 31/4045* (2006.01)

(52) U.S. Cl.
  CPC .................................. *C07D 209/14* (2013.01)

(58) Field of Classification Search
  None
  See application file for complete search history.

(56) References Cited

PUBLICATIONS

Begum, et al., Molecules, 15:68 (Dec. 28, 2009).*

* cited by examiner

*Primary Examiner* — Michael Barker
(74) *Attorney, Agent, or Firm* — Sarfaraz K. Niazi

(57) ABSTRACT

The present invention evaluated the anti-epileptogenic effect of tryptamine derivative HHL-6 and its effects on the expression of BDNF and c-Fos. HHL-6 possesses potent anticonvulsant and anti-epileptic activity in PTZ-induced acute seizure and chemical kindling model of epilepsy. The results suggests that one of the possible mechanism of HHL-6 to inhibit epileptogenesis might be due to its controlling effect on the cellular and molecular expression of the factors that contribute in the development of epileptogenic plasticity in the CNS.

3 Claims, 4 Drawing Sheets

MODULATION OF C-FOS AND BDNF PROTEIN EXPRESSION IN PENTYLENETETRAZOLE-KINDLED MICE FOLLOWING THE TREATMENT WITH NOVEL ANTI-EPILEPTIC COMPOUND HHL-6

BACKGROUND OF THE INVENTION

Epilepsy is a neurological disorder manifested by rapid and recurrent seizures, resulting from synchronized discharges of neurons in brain, affecting at least 1% of the world population To explain the mechanism how seizures are generated in specific brain areas or different brain structures, various studies have been performed worldwide involving behavioral, electrophysiological and molecular analysis. So far, the immense majority of epilepsy research has been executed in rodents and stimulation of neurons by electrical or chemical induction resulting in seizure discharges is believed to be the most common way to contribute to the process of epileptogenesis referred as "kindling."

In kindling, an initially sub-convulsive chemical or electrical convulsant stimulus of the brain evokes seizure discharges. The molecular mechanisms underlying the development of the abnormal excitability in kindling or epilepsy are poorly understood. However, it is believed that structural rearrangements responsible for maintenance of epileptic syndrome might be triggered by trophic factors such as BDNF (brain derived neurotrophic factor) that is involved in various signaling mechanisms that may be influenced by seizure activity. Among various trophic factors, much interest has been focused on the BDNF, NGF, and NT-3, and their high-affinity receptors TrkA, TrkB and TrkC. Variety of epilepsy models have shown that seizure activity induces transient changes of neurotrophin gene expression in neurons. In addition to these trophic factors, the proto-oncogene c-fos has also been shown to be induced transiently in response to various stimuli such as seizures induction. The c-fos gene encodes a DNA-binding protein, c-Fos, which forms a heterodimeric transcriptional factor, activator protein-1 (AP-1) by direct participation or with c-jun. The activation of c-fos expression in neurons by seizures led to its proposed use as a marker of neuronal activity.

BRIEF SUMMARY OF THE INVENTION

In the present invention, we used pentylenetetrazole (PTZ) to induce epileptogenesis in mice. The reason for using this chemoconvulsant was based on studies reporting that the PTZ dependant induction of c-fos expression might play an important role in the development of seizures and excitatory amino-acid induced toxicity. Thus, during the development of kindling, each stimulus-evoked seizure leads to increased expression of BDNF and c-fos resulting in seizure development. Due to the fact that BDNF and c-fos expression in neurons is transiently increased during seizures, we have used them as molecular indicators of neuronal activity in various brain regions to monitor the effect of our test compound, HHL-6.

DETAILED DESCRIPTION OF THE INVENTION

Albino male NMRI mice weighing 20-25 grams were used. The animals were housed under standard laboratory conditions i.e. 12:12 hr light: dark cycle, temperature (21±2° C.) and air humidity controlled environment. Food and water were provided ad libitum. All experiments were carried out in accordance to the International Guidelines for the Use and Care of Laboratory Animals and approved by Scientific Advisory Committee on Animal Care, Use, and Standards of our institute.

Figure 1:
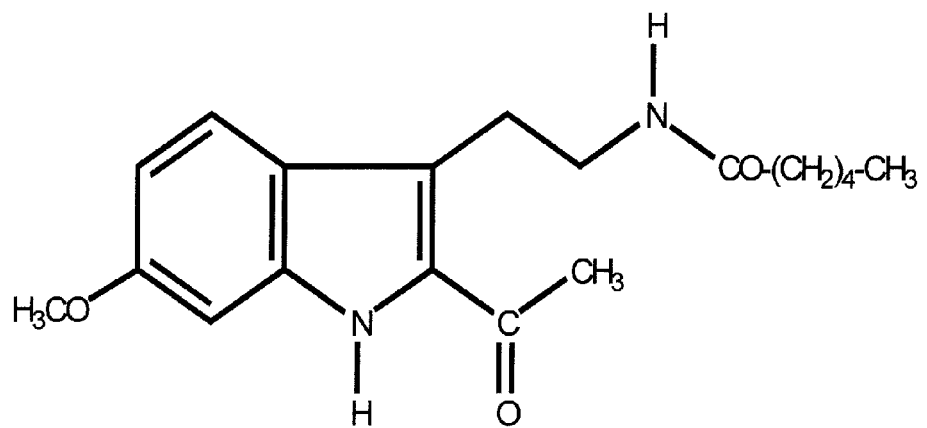
FIG. 1 depicts a structure of tryptamine derivative HHL-6 (2-acetyl-3-(2-hexanoylamidoethyl)-7-methoxyindole).

Pentylenetetrazole (PTZ) was used as a chemical convulsant whereas diazepam was used as a reference drug. The test compound HHL-6 (FIG. 1) was synthesized by our chemist collaborator at H.E.J. Research Institute of Chemistry, International Center for Chemical and Biological Sciences. Since the chemical convulsant PTZ is photosensitive, therefore, care was taken to prepare fresh PTZ solution on the day of administration without unnecessary exposure to the light. Primary antibodies i.e. purified c-Fos (4): sc-52 and BDNF (N-20): sc-546, were purchased from Santa Cruz Biotechnology (USA) and secondary antibody Alexa Flour® 488 goat anti-mouse IgG (H+L)*[2] were purchased from Invitrogen (USA)

Tables 1 and 2 outline the treatment regime followed for both the anticonvulsant and anti-epileptic activity testing of HHL-6.

TABLE 1

Treatment regime followed for subcutaneous PTZ-induced seizure test.

| Group | Treatment | Dose |
|---|---|---|
| GI | Normal Control | 0.2 ml of 0.9% Saline |
| GII | PTZ-Control | 90 mg/kg |
| GIII | Diazepam + PTZ | 7.5 mg/kg + 90 mg/kg |
| GIV | HHL-6 + PTZ | 20 mg/kg + 90 mg/kg |

TABLE 2

Treatment regime followed for PTZ-induced kindling test.

| Group | Treatment (administered on alternate days) | Dose |
|---|---|---|
| GI | Normal Control | 0.2 ml of 0.9% Saline |
| GII | PTZ-Control | 50 mg/kg |
| GIII | Diazepam + PTZ | 7.5 mg/kg + 50 mg/kg |
| GIV | HHL-6 + PTZ | 20 mg/kg + 50 mg/kg |

The anticonvulsant effect of HHL-6 using scPTZ test was evaluated by administering 20 mg/kg dose to groups of 6 mice at least 30 min before subcutaneous administration of convulsive dose of PTZ (90 mg/kg). After PTZ administration, animals were isolated and observed for an hour for the presence or absence of different types of seizure patterns. Latency to PTZ-induced threshold seizures was also calculated. The latency to threshold seizure is defined as the interval between the time of the PTZ-injection and the occurrence of first episode of threshold seizure. Protection of testing material against PTZ-induced mortality within 24 hours was also evaluated. In all experiments, diazepam (7.5 mg/kg i.p) was used as positive control.

Sub-convulsive dose (50 mg/kg) of PTZ was given subcutaneously to all groups (n=12/group) except normal control after every 48 hours. In normal control group, instead of PTZ, saline was used. The drug control groups received daily administration of diazepam (7.5 mg/kg). The test group was treated with the HHL-6 (20 mg/kg) once daily. Racine's scale was used to score the seizure activity such as stage 0: no response; stage 1: ear and facial twitching; stage 2: convulsive wave through the body; stage 3: myoclonic jerks, stage 4: clonic-tonic convulsions, turnover into side position; stage 5: generalized clonic-tonic seizures, loss of postural control. Animals showing score 4 or 5 were considered to be fully kindled.

Animals were transferred into individual cages the day before the experiments to allow them to acclimatize to the new environment. Animals were observed in these cages for 1-2 hr after drug treatment. Behavior (locomotion, head weaving, biting, licking or grooming, hyper excitability, ataxia and sedation, writhing, jumping etc.) of the animals was observed for 1-2 hr after they were injected with vehicle, standard drug and test sample. For behavioral studies, blind-testing was employed i.e., the experimenter conducting this study was blinded to the given treatment.

This was examined by Traction test. The forepaws of a mouse were placed on a small twisted wire rigidly supported above a bench top. Normal mice grasped the wire with forepaws and when allowed to hang free, placed at least one hind foot on the wire within 5 seconds. Inability to put up at least one hind foot constituted failure to the traction. The test was conducted at 30 min and 1 h after the injection of saline, diazepam or HHL-6.

Animals were sacrificed 24 hrs after establishment of complete kindling. Cardiac perfusion with chilled PBS buffer (NaCl—8 g, KCl—0.2 g, $Na_2HPO_4 \times 12$ $H_2O$—2.85 g, $KH_2PO_4$—0.2 g; pH 7.4) containing heparin was performed. Whole brains were removed, post-fixed in ice-cold 2% PFA for 24 hrs at +4° C. and then placed in 30% sucrose until brain samples sank to the bottom of the container. The samples were stored at −80° C. until further processing.

Frozen brain samples were cut into 30 μM thick sections and directly taken on poly L-lysine coated slides and kept at −20° C. overnight. The cryosections were incubated overnight at 4° C. with primary antibody i.e. purified c-Fos (4): sc-52 for c-Fos detection and BDNF (N-20): sc-546 for BDNF detection independently. This was followed by re-incubation with secondary antibody i.e. biotinylated goat anti-mouse IgG (Alexa Flour) for 1 hour at room temperature in dark. The stained sections were observed under fluorescent microscope (Nikon ECLIPSE TE2000-S, Japan). Since the specificity of the primary antibody is very critical therefore, in order to determine specificity, negative controls were also processed by eliminating the step where sections were incubated with their respective primary antibody.

Expression of c-Fos and BDNF protein observed under the fluorescent microscope was analyzed by using software ImageJ (NIH, USA). The image processing program ImageJ helps in multiple imaging system data comparisons taking density (densitometry) in consideration to analyze the images. For each image, background density was determined and subtracted; the remaining particles were considered to represent c-Fos or BDNF expression. Data were obtained from two sections per mouse (n=12 animals per group) and presented as means±S.E.M. cFos and BDNF immunoreactivity in the amygdala, cortex, dorsal hippocampus, and thalamus were centered approximately around 3.6 mm posterior to bregma. Within the hippocampus region, measurements were performed over the layer extending from sub-regions CA1-CA3.

Data is presented as mean±standard error of the mean (S.E.M.). The seizure activity was analyzed by nonparametric Mann-Whitney U tests. The immunostaining data was analyzed by one-way ANOVA with post hoc Dunnett's multiple comparison tests. Sequential differences among means were calculated at the level of $P<0.05$ using the SPSS version 10.

Figure 2:
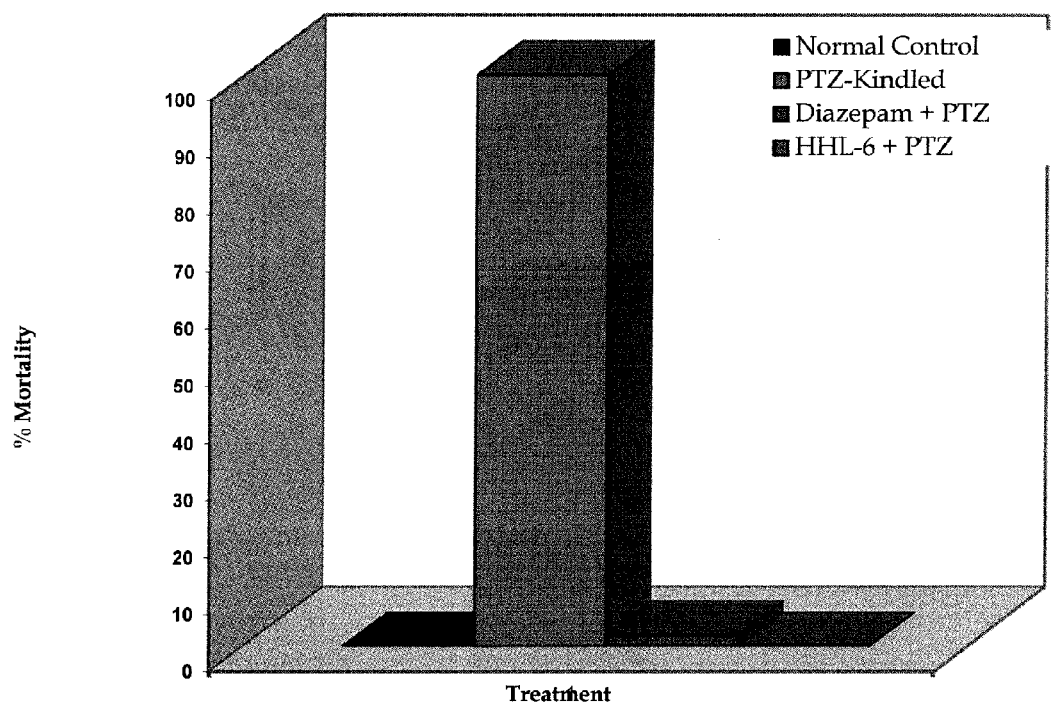
FIG. 2 depicts the percent mortality in different treated groups. Animals in the diazepam and HHL-6 treatment groups demonstrated 100% protection against scPTZ induced mortality.

The HHL-6 was unable to provide protection from jerks; however, the seizure behavior did not progress further. Moreover the latency to the onset of jerks was also delayed compared to PTZ control group. No rearing or falling was observed in the HHL-6 treated group compared to PTZ-control group (Table 3) and 100% protection from tonic fore limb and hind limb seizures was observed. In contrast, in PTZ-control group, once seizures were started these were more frequent and severe. In scPTZ test, 100% mortality was observed in PTZ-control animals only. Mortality was not demonstrated by groups receiving 20 mg/kg of HHL-6 or 7.5 mg/kg of diazepam (FIG. 2).

TABLE 3

Effect of HHL-6 on the duration and
inhibition of seizure in scPTZ-induced seizure in mice.

| Group | Dose | Onset of jerks (sec) | Rearing & falling (sec) |
|---|---|---|---|
| GI (Normal Control) | 0.2 ml/kg | 0 | 0 |
| GII (PTZ-Control) | 90 mg/kg | 190 | 640 |
| GIII (Diazepam + PTZ) | 7.5 mg/kg | 0 | 0 |
| GIV (HHL-6 + PTZ) | 20 mg/kg | 460 | 0 |

In Table 3, the HHL-6 and diazepam were injected intraperitoneally 30 min before the administration of subcutaneous pentylenetetrazole (90 mg/kg) in their respective groups. Values are presented as mean for the duration of tonic seizure for 6 mice.

Figure 3:
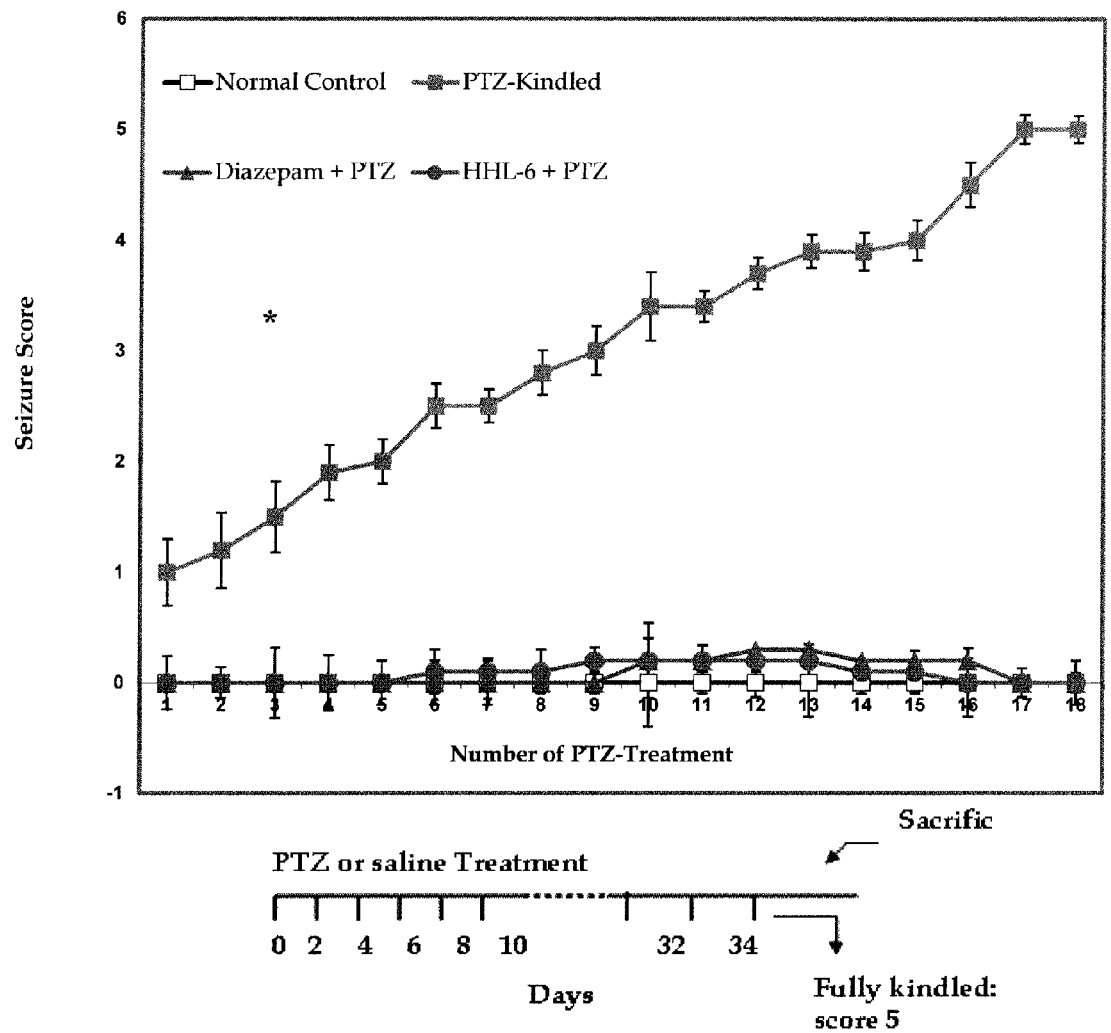
FIG. 3 depicts the effect of HHL-6 on scPTZ-induced kindling. The kindling scores are expressed as the arithmetic mean±SEM (n=12/group). The treatment of 20 mg/kg of HHL-6 showed a slight increase in their seizure score from treatment day 9 to 13 and thereafter it returned to the 0. The bar under the figure represents the timeline of the experiments. The mice were treated with PTZ or saline on alternate days. A total of 18 doses were given during the 36-days period when animals in control group were fully kindled. The average scores of PTZ-induced seizures were significantly higher in the kindled control mice (receiving no other treatment except PTZ). *$p<0.05$: significantly higher than normal control revealed by nonparametric Mann-Whitney U tests. The animals were sacrificed for immunohistochemistry and RT-PCR analysis after 36 days.
Figure 4A:
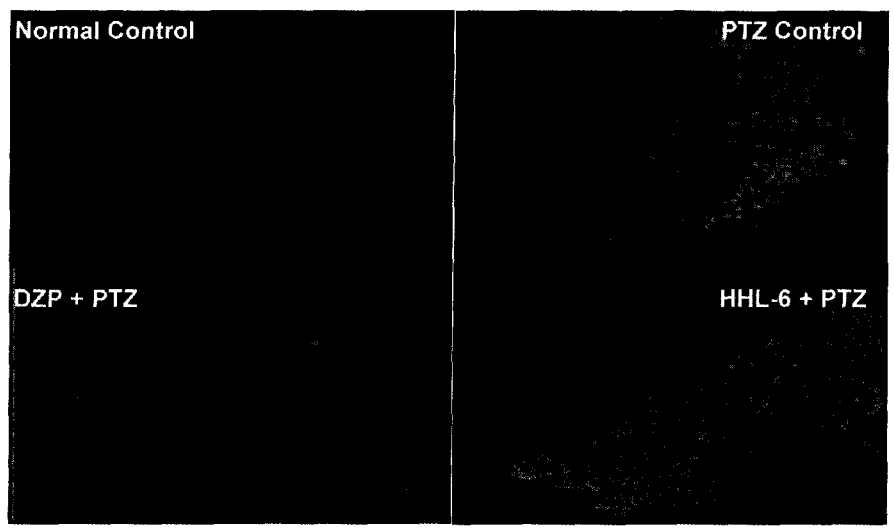
FIG. 4A depicts photomicrograph of c-Fos immunoreactivity in cortical region of normal and kindled mice brains with stage 5 seizure activity. Note the increased and scattered immunofluorescence in the PTZ-kindled control brain section. In contrast, the immunoreactivity of c-Fos in the brain of the kindled animals treated with HHL-6 and diazepam was markedly reduced.
Figure 4B:
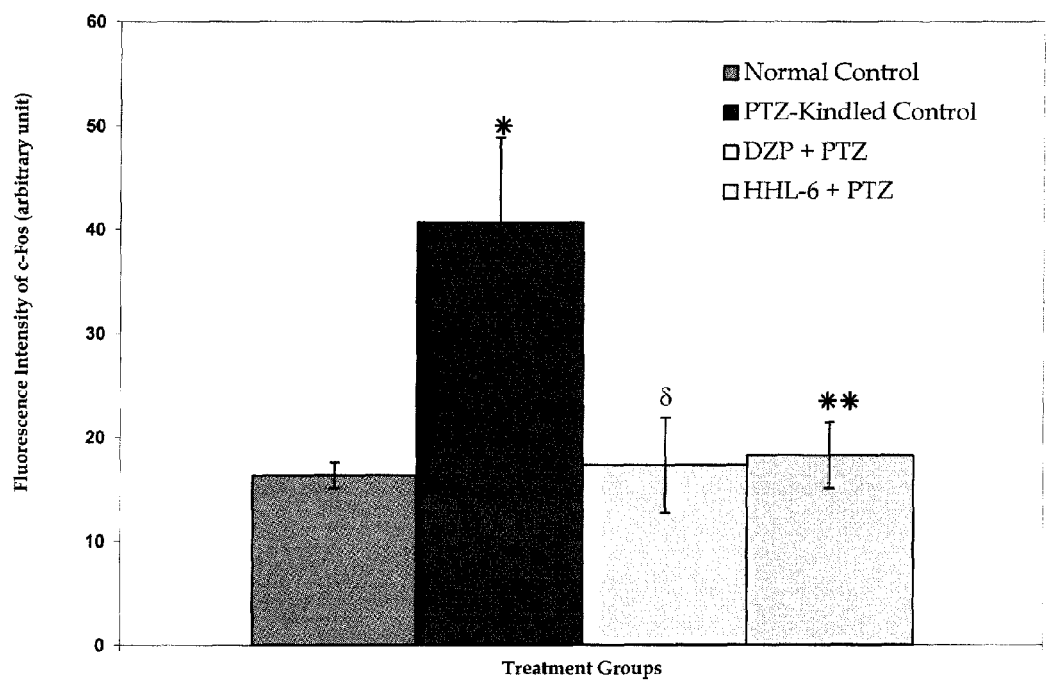
FIG. 4B depicts a graphical representation of the level of expression of immunohistochemically detected c-Fos in kindled and unkindled brain sections analyzed by ImageJ software. In comparison to the normal control group (16.31±1.24), the PTZ control animals showed a significant increase in the c-Fos staining intensity (40.69±8.2, *$p<0.001$). In contrast, c-Fos expression in the kindled animals treated with HHL-6 (18.24±3.2, **$p<0.01$) and diazepam (17.28±4.6, $^\delta p<0.05$) declines significantly.

The animals in scPTZ-kindled control group displayed a gradual increase in the seizure score reaching to score 5 after 18 treatments with an average seizure score of 4.9. Compared to PTZ-kindled control group, the diazepam treated group did not exhibit any seizure pattern till the end of the kindling protocol, however, a slight non-significant score of 0.3 was observed in case of HHL-6 group at the tested dose during treatment day 9 till 13, thereafter it completely retarded the development of kindling induced by scPTZ administration (FIG. 3). Within the treatment groups, no difference was found in the diazepam and HHL-6 treated animals.

Animals treated with HHL-6 did not show any alteration in their normal behavior pattern. Hyper-excitability or sedation was also not observed in the HHL-6 treated group.

The muscle relaxant activity was tested by traction test. We did not observed muscle relaxant activity of HHL-6 (20 mg/kg) in the treated animals. Since, we have used 20 mg/kg of HHL-6 in our kindling study therefore, in muscle relaxant activity analysis we did not increased the dose further.

In the normal control group, there was little to no immunoreactivity of c-Fos and BDNF. Immunohistochemical analysis revealed a significant increase in the expression of c-Fos protein in the brain sections of control PTZ-kindled mice ($P<0.001$) which was centered especially in the CA1-CA2 hippocampal region (3.6 mm posterior to the Bregma) and thalamus, when compared with the normal brain (Table 4). Within the cortex a relatively uniform distribution of cFos across all of the cortical layers was found. In contrast, the animals treated with diazepam (7.5 mg/kg, $p<0.05$) showed a significant reduction in the expression of c-Fos protein which was almost comparable to the normal control group.

TABLE 4

Fluorescence intensity of c-Fos (arbitrary unit) in
various regions of brain from normal and kindled mice.

| Brain Regions | Experimental Group | | | |
|---|---|---|---|---|
| | Normal Control | PTZ Control | DZP + PTZ | HHL-6 + PTZ |
| Amygdala | 12.23 ± 2.9 | 38.17 ± 5.08 | 14.94 ± 1.99 | 15.21 ± 2.3 |
| Cortex | 16.31 ± 1.24 | 40.69 ± 8.2 | 17.28 ± 3.6 | 18.24 ± 3.2 |
| Hippocampus | 15.29 ± 2.3 | 44.27 ± 7.43 | 20.09 ± 3.77 | 16.92 ± 2.75 |
| Thalamus | 12.58 ± 1.79 | 45.36 ± 3.70 | 18.33 ± 2.19 | 15.58 ± 3.74 |

Table 4 shows that significant increase in the expression of c-Fos protein in the brain sections of control PTZ-kindled mice ($P<0.001$) was centered especially in the hippocampal region followed by the thalamus. The HHL-6 treatment however reduces the expression of c-Fos in all four selected regions i.e., amygdala, cortex, hippocampus and thalamus.

Within the treatment groups, the brain sections from HLL-6 treated animals showed slightly more expression of c-Fos as compared to the diazepam treated kindled group, however, ANOVA with Dunnett's multiple comparison test analysis demonstrated that this difference was non-significant ($P<0.623$).

Figure 5A:
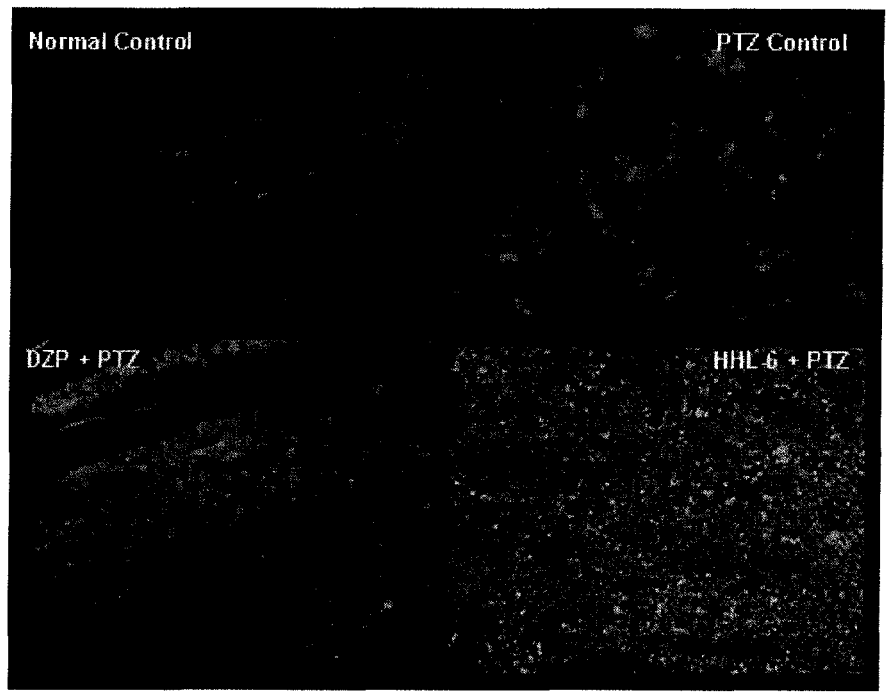
FIG. 5A depicts images of the BDNF immunoreactivity in cortical region of normal and kindled mice brains. A marked increased in the BDNF immunofluorescence was observed in the PTZ-kindled control brain section. In comparison to the PTZ control group, the immunoreactivity of BDNF in the brain sections of the kindled animals treated with HHL-6 and diazepam was markedly reduced.
Figure 5B:
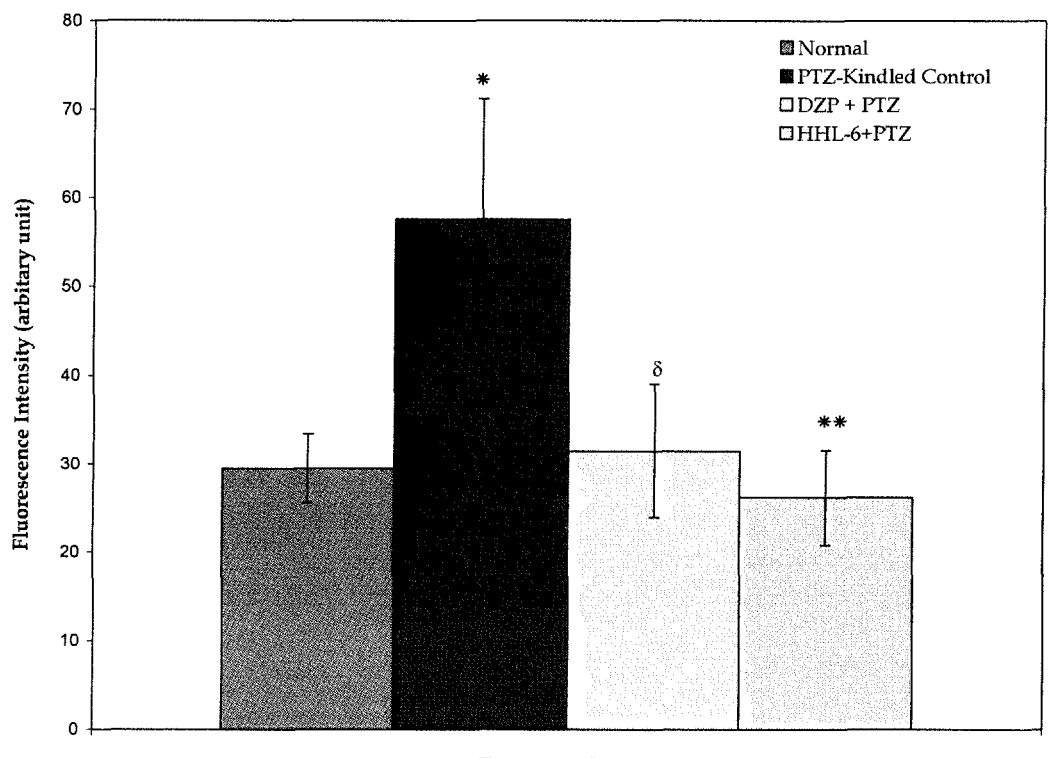
FIG. 5B depicts a graphical representation of the level of expression of immunohistochemically detected BDNF. The captured immuno-images were analyzed by ImageJ software. In comparison to the normal control group (29.53±3.9), the PTZ control animals showed a significant increase in the BDNF staining intensity (57.6±13.6, *$p<0.001$). In contrast, BDNF expression in the kindled animals treated with HHL-6 (26.2±5.4, **$p<0.003$) and diazepam (31.5±7.6, $\delta p<0.02$) declines significantly.

The BDNF immunohistochemical analysis of the brain sections from normal control animals reveals low levels of BDNF protein (FIGS. 5a and 5b). This distribution was indicative of BDNF protein-like immunoreactivity found in the mouse brain. In comparison to the normal control group, the PTZ-kindled control group has shown a marked increase in the expression of BDNF protein ($P<0.001$). Conversely, intriguing results were seen by our test compound HLL-6 (a tryptamine derivative) on the expression of BDNF protein as compared to standard anti-epileptic drug such as diazepam in PTZ kindled mice. The ANOVA analysis demonstrated that the reduction in the BDNF in HHL-6 treated group was significantly different from PTZ-kindled control group ($P<0.004$).

Well-defined seizure behaviors in kindling were initially reported and clearly illustrated by Racine and his team. The systemic administration of PTZ results in well-established generalized tonic-clonic seizures providing a good evidence to study epileptogenesis in mice. In addition to screening drugs against the disease, it also provides the basic experimental tool to study the underlying cellular or molecular mechanisms of the disease. In the present study, the PTZ exerted its convulsant effects in both acute and chronic models that were profoundly reversed by tryptamine derivative HHL-6 (20 mg/kg dose).

HHL-6 gave significant protection from mortality and forelimb and hind limb tonic extension in subcutaneous PTZ-induced seizure test. In addition, 20 mg/kg dose of HHL-6 was potent enough to retard the slow progression of seizure score when compared to PTZ control group resulting in significant protective effect of HHL-6 on the development of kindling process. These observations were in accordance to the previous studies involving the compounds having tryptamine derivatives or indole rings in their structures. Since, PTZ most likely produces seizures by inhibiting GABA neurotransmission specifically acting as $GABA_A$ receptor antagonist, the drugs preventing convulsions and seizures in PTZ treated mice or increasing the latency to seizures may work either by enhancing GABA activity or antagonizing glutamate neurotransmission. Since HHL-6 effectively retards seizures in PTZ-induced seizure model and development of epileptogenesis in PTZ-kindled mice, therefore we suggest that it might be acting through enhancing GABA activity. However, further confirmation will be verified by performing studies on GABA receptors levels or by doing molecular studies involving gene expression for GABA.

In addition to these seizure related behavioral changes, there are various underlying cellular and molecular factors which are reported to be involved in the process of epileptogenesis such as c-Fos and BDNF [35-38]. The immunohistochemical analysis of the brain sections prepared from the kindled mice brain revealed that experimentally induced epilepsy elicited collateral expression of c-Fos protein in amygdala, cortex, hippocampus, and thalamus. The densitometry data of hippocampal CA1-CA3 regions were further analyzed using ImageJ analysis.

Presently, we report that the tryptamine derivative HHL-6 and the reference drug diazepam greatly diminished the c-Fos protein expression showing no difference within these two groups. Our results further conform to the studies suggesting the proposed value of c-Fos in the modification in structure and function of neurons in mammalian nervous system to help define those brain structures that become activated by stimulation. Since, in earlier studies, it has also been reported that a single injection of PTZ (45 mg/kg) to mice, induced c-fos expression in several brain regions including the cerebral cortex and hippocampus. Therefore, it has been suggested that induction of c-Fos expression might play an important role in the development of seizures as well as in excitatory amino-acid induced toxicity. Hence, one of the purposes of this study was to determine whether the kindling induced over expression of c-Fos protein was fundamentally modulated by our test compound HHL-6 or not. Our results show concordance approach to previous studies involving c-Fos over expression in different models of neuronal stimulation and epilepsy. Interestingly, our test compound HHL-6 significantly reduces the expression of c-Fos in PTZ-treated mice as compared to normal control group providing potential antiepileptic effect.

Besides c-Fos, we also found a marked difference in the BDNF expression in the brain samples from normal control and PTZ-kindled control groups. Evidences demonstrate that epilepsy influences on the expression of BDNF both at mRNA and BDNF protein levels probably due to modulation of excitatory and inhibitory neurotransmission. Furthermore, studies have suggested that increased production of endogenous BDNF protein after a brain insult may be an important mediator of the cellular events that lead to the development of spontaneous seizures or epileptogenesis. Additional evidence puts forward the suggestion that limbic seizures can induce 4 to 10 fold increases in BDNF expression and this increased expression of BDNF is not only associated with increased seizure severity but it also induces various plastic changes in hippocampal neurons through activation of its receptor TrkB. Moreover, it was reported that BDNF is a must for signaling through TrkB receptors for kindling along with the fact that suppression of BDNF suppresses epileptogenesis. Induction of c-Fos and BDNF is also preceded by activation of second messenger cascades like the MAP-kinase pathway most likely resulting in the phosphorylation and activation of CREB protein. All of these studies are in line with our results that further confirm this up-regulation of BDNF protein in the kindled brain samples. Interestingly our test compound was found to reduce the expression of BDNF which was comparable to the normal control group suggesting its probable antiepileptic action. The speculation that BDNF might regulate its own synthesis leading to reduced BDNF signaling through down-regulated TrkB receptors also supports our data. On the other hand, an additional piece of evidence establishes that TrkB is required for limbic epileptogenesis but not BDNF suggesting the ligand independent activation of TrkB receptors. Therefore, next we will test the HHL-6 effects on the TrkB receptors to further identify the exact role of BDNF or its receptors (TrkA and TrkB) in the process of epileptogenesis.

There is clear indication of significant retardation in the process of epileptogenesis by HHL-6 in vivo both in acute and chronic models. In addition, alteration in c-Fos and BDNF expressions in different brain regions provide a sensitive measure to elicit kindling behavior in mice and HHL-6 greatly modulates this over expression suggesting its effective anticonvulsant and antiepileptogenic effect. This further emphasizes the need to confirm the activation of different neuronal pathways with different types of seizures by the help of additional molecular studies on receptor level.

What is claimed is:

1. A method of treating epilepsy comprising administering 2-acetyl-3-(2-hexanoylamidoethyl)-7-methoxyindole in sufficient quantity to a patient in need of treatment.

2. A method of treating seizures comprising administering 2-acetyl-3-(2-hexanoylamidoethyl)-7-methoxyindole in sufficient quantity to a patient in need of treatment.

3. The method of claim 1 administered to patients needing treatment of epilepsy or seizures in a dose of 1-50 mg/kg.

* * * * *